United States Patent
Gattiglia

(10) Patent No.: US 6,655,315 B1
(45) Date of Patent: Dec. 2, 2003

(54) MOISTURE INDICATORS FOR THE ABSORBENT CAPACITY OF A DESICCANT

(75) Inventor: Marco Gattiglia, Chiusa San Michele (IT)

(73) Assignee: Levosil S.p.A., Chiusa San Michele (IT)

( * ) Notice: Subject to any disclaimer, the term of this patent is extended or adjusted under 35 U.S.C. 154(b) by 0 days.

(21) Appl. No.: 10/048,161

(22) PCT Filed: Jul. 26, 2000

(86) PCT No.: PCT/EP00/07141

§ 371 (c)(1),
(2), (4) Date: Jan. 29, 2002

(87) PCT Pub. No.: WO01/09601

PCT Pub. Date: Feb. 8, 2001

(30) Foreign Application Priority Data

Jul. 30, 1999 (IT) .......................................... MI99A1714

(51) Int. Cl.[7] .............................................. G01D 21/00
(52) U.S. Cl. ................ 116/206; 116/200; 116/DIG. 41; 73/74
(58) Field of Search ................................. 116/206, 400, 116/DIG. 41; 73/73

(56) References Cited

U.S. PATENT DOCUMENTS

| | | | | |
|---|---|---|---|---|
| 2,214,354 A | * | 9/1940 | Snelling | ...................... 116/206 |
| 2,249,867 A | | 7/1941 | Snelling | |
| 2,460,065 A | * | 1/1949 | Davis | .......................... 116/206 |
| 2,460,072 A | | 1/1949 | David | |
| 2,854,815 A | * | 10/1958 | Piquerez | ..................... 116/206 |
| 3,084,658 A | * | 4/1963 | Schell | ......................... 116/206 |
| 3,172,731 A | | 3/1965 | Hirschler | |
| 6,324,896 B1 | * | 12/2001 | Aoyagi et al. | .................. 73/73 |

FOREIGN PATENT DOCUMENTS

| | | | | |
|---|---|---|---|---|
| WO | WO 92/02801 | * | 2/1992 | .......... G01N/19/10 |
| WO | WO 92/02804 | | 2/1992 | |
| WO | WO 98/16821 | | 4/1998 | |

* cited by examiner

*Primary Examiner*—Christopher W. Fulton
*Assistant Examiner*—Amanda J Hoolahan
(74) *Attorney, Agent, or Firm*—Young & Thompson

(57) ABSTRACT

Moisture indicators comprising, as active principle, copper chloride or another salt capable of releasing $Cu^{++}$ and $Cl^-$ ions, and synergistic salts containing chloride ions, which may be hygroscopic on a suitable support. Depending on the application, the support may be amorphous silica or silica gel; a solid paper support for making a moisture-indicating label; or a bentonite or calcium sulphate for making pellets by mechanical pressing.

11 Claims, No Drawings

MOISTURE INDICATORS FOR THE ABSORBENT CAPACITY OF A DESICCANT

BACKGROUND OF THE INVENTION

The present invention relates to moisture indicators capable of indicating the absorbent capacity of a desiccant material or more generally the moisture conditions present in the medium in which the indicator is placed.

The moisture indicators according to the invention comprise an active principle which is used in particular for colouring amorphous silica or silica gel, for colouring solid supports in the form of labels or for colouring bentonite or calcium sulphate pellets, or for impregnating molecular sieves, alumina, fossil flour, diatomaceous earth or the like.

The main types of solid static desiccants that are commercially available are silica gel, bentonites, molecular sieves and alumina.

The main applications are:

Dehydration of industrial liquids and gases.

Protection of materials, chemical products and pharmaceuticals, metal parts and electronic circuits against atmospheric moisture, using desiccant sachets, packets or capsules placed inside the protective packaging.

Drying of air in electrical apparatus and in transformers.

It is always necessary to demonstrate the absorbent capacity of the desiccant material, not only at the time of the first sale but also at the time of use.

For these reasons, in any application in which it is necessary to rigorously test the desiccant power of silica, blue silica gel is used (amorphous silica containing 0.5% by weight of cobalt chloride).

Blue silica gel indicates when it is spent by changing colour from blue (maximum desiccant activity) to pink (inactive as a desiccant).

However, when products based on desiccant clay (material which shows no obvious differences between its maximum activity and depletion of the desiccant power) are packaged, moisture-indicating labels are introduced into the packaging. In this way, the purchaser of the product personally checks the desiccant activity of the material purchased.

In addition, these indicator labels are commonly used for indicating the moisture conditions present inside industrial packagings, thus pointing out any penetration of moisture into these packagings and revealing the ambient conditions present during transportation.

A portion of the area of the indicator labels is impregnated with a cobalt chloride solution. This zone changes colour from blue to pink depending on the moisture present in the medium in which the label is placed; the colour change is reversible and thus allows the label to be regenerated for further use.

The concentration of the cobalt chloride solution used for colouring the indicator labels determines the sensitivity to the various moisture contents and thus the possibility of changing from blue to red in the way complying most with the ambient conditions in which the moisture indicator is required to work.

In Amendment XXV of European Directive 67/548, the cobalt chloride used hitherto in the field of desiccant materials inside silica or on labels as a moisture indicator has been relabelled and reclassified.

The consequences of this regulation include a series of warnings as regards the handling and use of products containing inorganic cobalt salts.

Since in blue silica gel, in indicator labels and in bentonite pellets and similar support materials, the coloration is given by cobalt chloride at a certain concentration, the problem arises of identifying one or more components capable of replacing cobalt chloride in its function as a substance capable of changing colour according to atmospheric moisture.

It is this problem which it is the aim of the invention to solve, and thus to provide moisture indicators whose characteristics are at least equal to those currently existing, which make use of cobalt chloride.

SUMMARY OF THE INVENTION

Essentially, according to the invention, copper chloride ($CuCl_2$) is used as active principle in combination with a mixture of hygroscopic salts containing the chloride ion for the purpose of colouring solid supports which, besides optionally being desiccants, change colour according to the moisture present in the medium with which they are placed in contact.

In particular, with this active principle, the Applicant has developed a novel coloured silica gel whose moisture-absorbing capacities are no different to those of the previous silica gel, which can be regenerated without problems, and which undergoes a colour change from brown-yellow (when dry) to aquamarine (when wet).

In addition, with this active principle it has been possible to identify many different water-alcohol and aqueous mixtures which allow the production of moisture-indicator cards and dry mixtures of desiccant salts and materials so as to produce moisture-indicating desiccant pellets or manufactured products of any type having these characteristics.

DETAILED DESCRIPTION OF THE PREFERRED EMBODIMENTS

The invention will now be described in greater detail, with the aid of examples also, with reference to the fields of application mentioned above: silica gels, moisture-indicating labels, desiccant pellets.

COLOURED SILICA GEL

The novel coloured silica gel was obtained by impregnating silica gel with copper II chloride (indicated for simplicity as copper chloride or active principle, abbreviated to A.P.), combined with other synergistic salts.

PREPARATION

Coloured silica gel capable of changing colour when it passes from completely dehydrated to partially hydrated can be produced by replacing, during the industrial process designed for the production of blue silica gel, the cobalt chloride with a mixture of copper chloride and another synergistic salt which must principally contain chloride ions and optionally be hygroscopic.

The mixture of the invention, used for impregnating silica gel, consists of copper chloride coupled with various chloride salts and hygroscopic salts acting as synergists.

The mixture of the invention can optionally be improved by adding coloured salts, thus capable of modifying the coloration of the silica gel.

Following immersion of the white silica gel in a solution composed of the active principle and of its synergist, a material is generated which undergoes colour changes from yellow-brown when dry to aquamarine when wet.

The colour changes of the material obtained after impregnation with the mixture of the invention can be evaluated by exposing the material to different values of relative humidity in a climatic chamber.

Depending on the concentrations of the active principle and of the synergist in the mixture used for the impregnation, and as a function of the contact times between the mixture and the material to which a colour is given, a material that is more or less sensitive to moisture can be obtained, which thus undergoes the colour change from brown-yellow to blue aquamarine at different relative humidities.

Among the selected products with a synergistic function which may be used, for example, are the following hygroscopic or deliquescent chlorides:

magnesium chloride, lithium chloride, sodium chloride, calcium chloride, potassium chloride, barium chloride, ferric chloride or in general metal chlorides.

Among the synergistic salts not containing chloride ions which can nevertheless allow different colour shades for the silica gel, mention may be made(in the presence of copper ions), for example, of:

potassium nitrate, calcium nitrate, potassium acetate, magnesium nitrate, potassium dichromate, sodium bromide.

Examples of anions, introduced in the form of synergistic salts, which, in the presence of copper ions, provide a background coloration to the silica lo gel which is such that it modifies the coloration imparted by the active principle alone are:

bromide ions, dichromate ions, nitrate ions, sulphate ions.

The hygroscopic salts are used in amounts not greater than 30 times the amount of copper chloride.

The silica gel is impregnated by immersing it in solutions containing the active principle and its synergist. The white silica gel used for this operation can be completely dry, in which case subsequent rupture of the silica gel crystal takes place during the hydration and impregnation process, or precipitated silica gel still containing 90% water coordinated inside, which, after drying, reduces in size and weight to generate the silica gel commonly sold.

In general, silica gel still containing 90% water is immersed in an aqueous solution containing the active principle and its synergist for the time required to absorb the active principle and its synergist in an amount which ensures a finished product containing between 0.1% and 1.5% by weight of the active principle and up to 3% of its synergist. The solutions used to obtain these end results may be highly concentrated and allow short immersion times, or weakly concentrated with long immersion times.

It is thus clear that, depending on the starting silica gel, more or less concentrated solutions can be used.

A number of examples which can demonstrate more clearly the use of the active principle and its synergist will now be illustrated.

EXAMPLE 1

Preparation 7 solutions (E, F, G, H, I, L, and O) containing 1.5 grams of copper chloride active principle, 0.4 liters of water and various types of synergist were produced, 2 solutions containing the active principle alone at different concentrations (Solutions M and N) and one solution containing a larger amount both of the synergist and of the active principle (Solution P).

500 grams of amorphous precipitated silica containing 90% water were immersed in each solution, for a period of 24 hours.

The silica gel thus obtained was drained and dried in an oven at 120° C. for 24 hours.

The solutions were labelled alphabetically:

E) 1.5 grams of copper chloride, 3.0 grams of potassium nitrate, 400 ml of water, F) 1.5 grams of copper chloride, 7.7 grams of magnesium nitrate, 400 ml of water, G) 1.5 grams of copper chloride, 2.5 grams of lithium chloride, 400 ml of water, H) 1.5 grams of copper chloride, 4.4 grams of calcium chloride, 400 ml of water, I) 1.5 grams of copper chloride, 3.5 grams of sodium chloride, 400 ml of water, L) 1.5 grams of copper chloride, 4.5 grams of potassium chloride, 400 ml of water, M) 1.5 grams of copper chloride and 400 ml of water without any synergist, N) 5 grams of copper chloride, 400 ml of water without any synergist, O) 1.5 grams of copper chloride, 6 grams of magnesium chloride, 400 ml of water, P) 5 grams of copper chloride, 20 grams of magnesium chloride, 400 ml of water.

Table summarising the experimental mixtures:

TABLE

| Solution | Active principle | Grams of synergist | Solvent and grams of silica containing 90% water | Dry coloration | Wet coloration |
|---|---|---|---|---|---|
| E | 1.5 grams | $KNO_3$ 3.0 grams | 400 ml water/ 500 g wet silica | Apple green | Aquamarine green |
| F | 1.5 grams | $Mg(NO_3)_2 \cdot 6\,H_2O$ 7.7 grams | 400 ml water/ 500 g wet silica | Apple green | Blue |
| G | 1.5 grams | LiCl 2.5 grams | 400 ml water/ 500 g wet silica | Brown-yellow | Light aquamarine green |
| H | 1.5 grams | $CaCl_2 \cdot 2\,H_2O$ 4.4 grams | 400 ml water/ 500 g wet silica | Greenish-yellow | Light aquamarine green |
| I | 1.5 grams | NaCl 3.5 grams | 400 ml water/ 500 g wet silica | Ash-yellow | Light aquamarine green |

TABLE-continued

| Solution | Active principle | Grams of synergist | Solvent and grams of silica containing 90% water | Dry coloration | Wet coloration |
|---|---|---|---|---|---|
| L | 1.5 grams | KCl 4.5 grams | 400 ml water/ 500 g wet silica | Dark yellow | Aquamarine green |
| M | 1.5 grams | — | 400 ml water/ 500 g wet silica | Olive green | Light blue |
| N | 5 grams | — | 400 ml water/ 500 g wet silica | Brown/dark green | Aquamarine green/blue |
| O | 1.5 grams | $MgCl_2 * 6H_2O$ 6 grams | 400 ml water/ 500 g wet silica | Yellow-brown | Light blue |

Results:

Silicas M and N, produced by immersing the silica gel in solutions of the active principle (A.P.) alone give dry-coloration shades ranging from olive green to dark green tending towards black.

By immersing the silica in solutions containing, besides the active principle, various synergists containing chloride ions, such as: lithium chloride, calcium chloride, magnesium chloride, sodium chloride and potassium chloride, and using a constant amount of A.P. (e.g.: G, H, I, L, O), silicas are obtained coloured yellow with various shades thereof.

The importance of having the chloride ions introduced by means of the synergist, in the colour change of the silica depending on the moisture contained in the material, may thus be deduced. Specifically, the silica obtained with the A.P. alone is olive green in colour when dry, while the silica with the same amount of A.P. and 0.06 mol of chloride ions added in solution by means of the synergist generates a silica with a yellow-brown shade when dry.

The various shades of yellow can be attributed to the presence of the different type of cation.

Silica produced following immersion in solutions containing the same amount of A.P. and a synergist containing one of the cations used previously (magnesium and potassium) but having a nitrate anion instead of a chloride anion (Solutions E and F), is apple green in colour when dry, (different shade from the olive green of the dry silica made with the A.P. alone), the difference probably being attributable to the formation, inside the silica, of copper nitrate whose blue coloration contributes towards changing the colour of the dry silica from olive green to apple green.

It is possible by the same principle to change the coloration of the olive green or yellow silica by means of synergists which provide in solution anions other than chloride ions and which form with the copper, salts having particular colorations. The addition of the previous coloration to the colour of the salt formed by means of the synergist results in particular shades:

Experiments were carried out on this point by attempting impregnations of silica by means of solutions containing copper sulphate with the addition of a synergist containing chloride ions, or starting with solutions containing sulphate ions, introduced via any salt thereof, and copper chloride. In these cases, the formation of copper sulphate gives rise to different shades for equal doses of chloride ions and under the conditions described previously.

In general, any coloured copper salt can be used, such as, for example:

Copper(II) bromide—dark green coloration
Copper(II) dichromate—black coloration
Copper(II) nitrate—blue coloration
Copper(II) sulphate—blue coloration A similar but inverted approach may be taken, for example using the active principle to which is added a synergist containing chloride ions, but also introducing into the silica very small amounts of inorganic salts or compounds of other nature so as to provide cations which form coloured salts with the chloride ions.

The colorations of the silicas obtained by means of immersion in the solutions studied previously are then varied as a result of the contribution made by the new coloured salt. E.g.:

By introducing small amounts of the following cations into the starting silica or into the solutions used for the impregnation, the following coloured salts can be obtained inside the silica, which interfere with the coloration obtained in the previous experiments:

| Cation introduced into the silica | Salt formed in the presence of chloride ions | Colour of the salt formed in the presence of chloride ions |
|---|---|---|
| Iron(II) | Ferrous chloride | Green |
| Iron(III) | Ferric chloride | Brown |
| Chromium(III) | Chromium(III) chloride | Violet |
| Manganese(II) | Manganese chloride | Pink |

An example of this type can be obtained by impregnating 500 grams of amorphous silica containing 90% water with one of the solutions described previously to which an amount of less than one gram of ferric chloride is added.

To demonstrate even more clearly the fundamental action of the synergist, mixtures of active principle and of conventional synergists were prepared in ratios different to those described previously.

When the silica is impregnated with the following solutions, which contain twice as much synergist as previously, the following colorations are obtained:

| Solution | Active principle | Grams of synergist | ml of solvent and grams of 90% wet silica | Dry coloration | Wet coloration |
|---|---|---|---|---|---|
| E/1 | 1.5 | $KNO_3$ 6.0 grams | 400 ml water/ 500 g wet silica | Apple green | Bright aquamarine green |
| F/1 | 1.5 | $Mg(NO_3)_2 * 6 H_2O$ 15.4 | 400 ml water/ 500 g wet silica | Bright apple green | Blue |

-continued

| Solution | Active principle | Grams of synergist | ml of solvent and grams of 90% wet silica | Dry coloration | Wet coloration |
|---|---|---|---|---|---|
| G/1 | 1.5 | grams LiCl 5 grams | 400 ml water/ 500 g wet silica | Yellow | Yellowish aquamarine green |
| H/1 | 1.5 | CaCl$_2$ . 2 H$_2$O 8.8 grams | 400 ml water/ 500 g wet silica | Ash green-yellow | Aquamarine green |
| I/1 | 1.5 | NaCl 7 grams | 400 ml water/ 500 g wet silica | Dull lemon yellow | Pale aquamarine green |
| L/1 | 1.5 | KCl 9 grams | 400 ml water/ 500 g wet silica | Yellow | Pea aquamarine green |

By immersing amorphous silica (containing 90% water) for 24 hours in the solutions described above, a coloured silica gel is obtained which, when dried for 24 hours in an oven at 120° C., decreases in size and weight to generate the silica gel commonly used as a desiccant.

By doubling the amount of synergist, it is possible to observe its influence on coloration and sensitivity to colour change of the impregnated silica gel after exposure for a few hours in a climatic chamber to different relative humidities.

In general, the amount of copper chloride active principle in the silica gel can be as much as 2%, but if it is desired to obtain moisture-sensitive solutions, the amounts used should be about 0.2% by weight of active principle and up to 2% by weight of synergist.

To demonstrate the possibility of using copper salts other than copper chloride, coloured silica was prepared starting with copper sulphate.

EXAMPLE 2

Solution "S":

6 grams of copper sulphate+6 grams of magnesium chloride, 150 ml of water, 100 grams of dry white silica gel.

In this case, use was made of common commercially available dry silica gel with a water content of about 2%, by immersing it in the solution S described above for about one minute.

After the silica gel impregnated according to this method has been dried, it can be seen that the coloured silica gel obtained changes colour from brown-yellow to blue acquamarine according to the amount of moisture it has absorbed.

The possibility of obtaining these results by starting with general copper salts in solution with general salts containing chloride ions is made possible by the fact that the active mixtures require in solution the presence of copper (II) ions together with chloride ions, plus optionally ions derived from the dissolution of the hygroscopic or deliquescent general salts added, and the copper and chloride counterions introduced previously. In general, more vivid colorations can also be obtained just by using hydrochloric acid as synergist, as can be seen from the example which follows.

EXAMPLE 3

Solution I:

0.01 mol of copper sulphate+0.02 mol of chloride ions (derived from diluted hydrochloric acid)+potassium nitrate, 100 ml of water and 100 grams of dry white silica gel Solution II:

0.01 mol of copper sulphate, 0.01 mol of magnesium chloride, 100 ml of water and 100 grams of dry white silica gel.

The two mixtures produce similar results since they generate similar concentrations of active principle in solution.

On investigating equeous solutions of the active principle and of its synergist at various pH values, no differences in activity were encountered as long as no copper hydroxide precipitated out, which would inhibit the possibility of there being colour changes. In addition, to produce the solutions used to impregnate the silica gel, any solvent capable of giving the active principle even slight solubility without adversely affecting the formation of the coloured silica can be used. Dilute inorganic acids, aqueous solutions, aqueous-alcoholic solutions or alcoholic solutions can thus be used.

Other static desiccant materials, for example alumina, can be impregnated by the same method.

INDICATOR LABELS

The indicator labels consist of a paper support soaked in or sprayed with aqueous-alcoholic or aqueous solutions of the copper chloride active principle mixed with deliquescent hygroscopic salts or with salts containing chloride ions.

The paper is then dried with a jet of hot air or by heating in a normal oven at about 70° C. for the time required.

Solutions at various concentrations of the active principle alone or combined with the other synergistic salts were used in order to control the colour change as a function of the moisture to which the paper should be sensitive.

The active principle, investigated on many different types of paper support, can be used to impregnate various supports such as natural fabrics, synthetic nonwoven fabrics, and in general any fabric used in the field of packaging desiccants.

When the paper produced by immersion in the solutions described is exposed to a dry medium, it is generally yellow in colour, whereas, when placed in a humid medium, it changes colour to colourless or blue acquamarine.

EXAMPLE 4

Various solutions of the active principle combined with other synergistic salts were prepared in order to check the various colorations of the indicator labels produced by means of impregnation, and to reveal the differences encountered when solutions containing the active principle alone or the active principle in the presence of synergists are used.

A) 1.5 g of COPPER CHLORIDE (dihydrate)+0.04 mol of anhydrous POTASSIUM NITRATE+100 ml of water B) 1.5 g of COPPER CHLORIDE+0.04 mol of MAGNESIUM NITRATE (hexahydrate)+100 ml of water C) 1.5 g of COPPER CHLORIDE+0.02 mol of MAGNESIUM CHLORIDE (hexahydrate)+100 ml of water D) 1.5 g of COPPER CHLORIDE+0.04 mol of LITHIUM CHLORIDE (anhydrous)+100 ml of water E) 1.5 g of COPPER CHLORIDE+0.08 mol of LITHIUM CHLORIDE (anhydrous)+100 ml of water F) 1.5 g of COPPER CHLORIDE+0.02 mol of CALCIUM CHLORIDE (dihydrate)+100 ml of water G) 1.5 g of COPPER CHLORIDE+100 ml of water ) 1.5 g of COPPER CHLORIDE+10 grams of POTASSIUM NITRATE (anhydrous)+4 grams of MAGNESIUM CHLORIDE+100 ml of water The differences in effect with solutions containing magnesium chloride as hygroscopic synergist were also studied.

H) 1.5 g of COPPER CHLORIDE+8 grams of MAGNESIUM CHLORIDE+100 ml of water

I) 1.5 g of COPPER CHLORIDE+10 grams of MAGNESIUM CHLORIDE (hexahydrate)+100 ml of water J) 1.5 g of COPPER CHLORIDE+1 gram of MAGNESIUM CHLORIDE (hexahydrate)+100 ml of water After proceeding as described previously, the following results were obtained:

comparing the effects of solutions H, I and J containing, in addition to the active principle, magnesium chloride in various proportions, it is observed that the papers immersed in solutions H and I and then dried with hot air acquire a bright yellow colour, while the papers obtained by immersion in solution J have a less bright yellow colour. The different sensitivity to atmospheric moisture can also be ascertained.

When the results obtained by immersing the paper in solutions B, C, G and K are compared, the following differences may be observed:

The paper impregnated with solution G, based on copper chloride alone without the addition of synergists, has a yellow colour when dry which is less intense than the colour of the papers impregnated with mixtures of the active principle and of its synergist containing chloride ions.

The paper obtained after immersion in solution B, containing magnesium nitrate, is blue acquamarine when wet, changing to greenish-yellow when dry. In this case, the synergist does not provide chloride ions but increases the presence of the nitrate ions with a reinforcement of the light blue colour when wet by virtue of the formation of copper nitrate, in a similar manner to that explained with reference to the silica gel.

The papers produced by immersion in solution C give a very bright yellow in a dry medium, whereas by immersion in solution K, ash-yellow papers are obtained due to the contribution of the synergist based on chloride ions mediated by the synergist based on nitrate ions.

After drying the papers impregnated by the method described, they can be exposed to a humidity equal to 40% and 23° C., thus producing various colour changes which can be summarized by the following table:

| Colour of the paper in dry medium | Change after exposure for 1 hour in a climatic chamber at 40% RH, 23° C. | Colour obtained after exposure in a climatic chamber for 1 hour |
| --- | --- | --- |
| Paper impregnated with solution G: YELLOW | Complete change | Aquamarine green |
| Paper impregnated with solution B: YELLOW-GREEN | Complete change | Pale light blue |
| Paper impregnated with solution K: ASH-YELLOW | Partial change | Yellow-green |
| Paper impregnated with solution C: BRIGHT YELLOW | No change | Bright yellow |

By varying the amount or by varying the proportions between the active principle and the synergist, the colour changes can be controlled so as to give the indicator greater moisture sensitivity.

In order to obtain a change in the sample obtained by immersion in solution C and K, these papers should be exposed to a relative humidity greater than 40%.

Solutions D and E containing lithium chloride produce paper with a typical yellow colour when dry, but the difference in intensity due to the presence of different concentrations of synergist for an equal amount of active principle may be observed.

Similar comments may be made by comparing the papers obtained by impregnation in other solutions.

As has been stated previously, it is also possible to obtain the active principle by starting with copper salts other than copper chloride. In fact, it suffices to dissolve copper ions and chloride ions irrespective of their origin, as has already been ascertained in the production of coloured silica.

EXAMPLE 5

A mixture of copper sulphate pentahydrate and magnesium chloride was used.

3 grams of copper sulphate pentahydrate+5 grams of magnesium chloride hexahydrate in 100 ml of water.

The colours of the labels obtained reflect the colour changes of those obtained with the active principle normally used.

It is generally possible to generate moisture-indicating labels by starting with mixtures containing less than 1 grams per liter of the active principle and the 20 grams per liter of the synergist, up to the use of solutions containing 50 grams of active principle and four times the amount of synergist containing chloride ions.

The solutions were produced using aqueous-alcoholic or aqueous solvent mixtures, and the experiment was carried out on paper normally used to make the indicator labels sold by the Applicant.

The experiments can be reproduced, taking into account the differences in moisture sensitivity and colour shade caused by the different composition of the paper, while remaining clearly able to demonstrate the differences in colour shade.

MOISTURE-INDICATING PELLETS AND MANUFACTURED ARTICLES

A number of specific processing operations in the field of desiccants involve the use of pellets made of clay or made with calcium sulphate, which are used for protecting particular articles against moisture and for indicating the moisture present in a given medium.

By using copper chloride and optionally hygroscopic salts or general salts containing chloride ions, it is possible to obtain pellets or other articles, for example figurines, which, besides being desiccants, change colour depending on the moisture in the medium with which they come into contact.

EXAMPLE 6

Using copper chloride mixed with bentonites of fine particle size and magnesium stearate, indicator pellets having the composition below were obtained:

15 kg of fine bentonites, 1 kg of magnesium stearate, 1 kg of copper chloride, 0.5 kg of magnesium chloride.

Alternatively, humid calcium sulphate can be used as support in replacement for the bentonites, and subsequently mixed with the active principle and the synergist. The material is given the desired shape either by pressing or moulding, and is then dried. The product obtained is brown when dry, but blue when exposed to moisture.

Various support materials can be used instead of bentonites, such as, for example, molecular sieves, fossil flour or diatomaceous earth.

In each case, the mixtures described previously consisting of the active principle, the hygroscopic salts and the optional chloride-containing salts can be used.

What is claimed is:

1. Moisture indicator comprising a support coloured with copper chloride or one or more salts capable of releasing $Cu^{++}$ ions and $Cl^-$ ions, and one or more metal chlorides or synergistic hygroscopic salt.

2. Moisture indicator according to claim 1, in which said support is a desiccant material.

3. Moisture indicator according to claim 1, in which said support is amorphous silica or silica gel.

4. Moisture indicator according to claim 1, in which said support is a paper label, or alternatively is a natural fabric, a nonwoven fabric.

5. Moisture indicator comprising a support coloured with copper chloride or one or more salts capable of releasing $Cu^{++}$ ions and $Cl^-$ ions, and one or more metal chlorides or synergistic hygroscopic salt, wherein said support consists of bentonites of fine particle size or calcium sulphate, molecular sieves, fossil flour, diatomaceous earth or alumina.

6. Moisture indicator according to claim 5, characterized in that it is in the form of moisture-indicating pellets.

7. Moisture indicator according to claim 5, characterized in that it is in the form of figurines or artistic manufactured products.

8. Moisture indicator according to claim 1, in which the synergistic hygroscopic salts are selected from bromides, dichromates, nitrates and sulfates.

9. Moisture indicator according to claim 1, in which the synergistic hygroscopic salts are selected from magnesium chloride, lithium chloride, sodium chloride, calcium, chloride, potassium chloride, barium chloride, ferric chloride, potassium nitrate, calcium nitrate, potassium acetate, magnesium nitrate, sodium sulphate, sodium bromide, potassium dichromate.

10. Moisture indicator comprising a support coloured with copper chloride or one or more salts capable of releasing $Cu^{++}$ ions and $Cl^-$ ions, and one or more metal chlorides or synergistic hygroscopic salt, wherein said hygroscopic salts are in amounts not greater than 30 times the amount of copper chloride.

11. A moisture indicator comprising:

at least one salt capable of releasing $Cu^{++}$ ions and $Cl^-$ ions and being between 0.1% and 1.5% by weight of the moisture indicator;

at least one of a metal chloride and a synergistic hygroscopic salt; and a support, said at least one salt and said synergistic salt coloring said support.

* * * * *